US012768848B2

(12) United States Patent
Julien

(10) Patent No.: US 12,768,848 B2
(45) Date of Patent: Oct. 20, 2026

(54) FLUID MAA/SAA LEVELS AS MAMMAL MANAGEMENT TOOLS

(71) Applicant: William Julien, Omaha, NE (US)

(72) Inventor: William Julien, Omaha, NE (US)

(73) Assignee: William E. Julien, Omaha, NE (US)

( * ) Notice: Subject to any disclaimer, the term of this patent is extended or adjusted under 35 U.S.C. 154(b) by 577 days.

(21) Appl. No.: 18/276,895

(22) PCT Filed: Feb. 9, 2022

(86) PCT No.: PCT/US2022/015769
§ 371 (c)(1),
(2) Date: Aug. 11, 2023

(87) PCT Pub. No.: WO2022/173796
PCT Pub. Date: Aug. 18, 2022

(65) Prior Publication Data

US 2024/0118293 A1 Apr. 11, 2024

Related U.S. Application Data

(60) Provisional application No. 63/148,777, filed on Feb. 12, 2021, provisional application No. 63/148,778, filed on Feb. 12, 2021, provisional application No. 63/148,779, filed on Feb. 12, 2021, provisional application No. 63/148,789, filed on Feb. 12, 2021, provisional application No. 63/290,276, filed on Dec. 16, 2021.

(51) Int. Cl.
*G01N 33/92* (2006.01)
*A01K 67/02* (2006.01)

(52) U.S. Cl.
CPC .............. *G01N 33/92* (2013.01); *A01K 67/02* (2013.01); *G01N 2405/00* (2013.01)

(58) Field of Classification Search
CPC ...... G01N 33/92; G01N 33/68; G01N 33/689; G01N 2405/00; A01K 2227/101; A01K 67/02; A01J 5/0131; A01J 5/007
USPC .............................................. 436/63, 71, 86
See application file for complete search history.

(56) References Cited

U.S. PATENT DOCUMENTS

| | | | | |
|---|---|---|---|---|
| 7,569,338 B1 * | 8/2009 | McDonald | G01N 33/6893 | 435/7.1 |
| 2003/0170840 A1 | 9/2003 | McDonald et al. | | |
| 2005/0107315 A1 * | 5/2005 | McDonald | C07K 14/4711 | 435/325 |
| 2006/0024804 A9 * | 2/2006 | McDonald | A61P 1/04 | 435/325 |
| 2016/0310565 A1 * | 10/2016 | Bach Ariza | A61K 38/1709 | |
| 2024/0248102 A1 * | 7/2024 | Julien | G01N 33/92 | |

OTHER PUBLICATIONS

H. Timur et al, "A study on the association between serum amyloid A and sperm concentration", First International Journal of Andrology, 2015, pp. 1-5.
International Search Report issued Jun. 8, 2022 in PCT/US2022/015769, 4 pages.
Mohammadreza Taghdiri et al, "Study on the accuracy of milk amyloid A test and other diagnostic methods for identification of milk quality", Veterinary Research Forum, 2018, 9(2), pp. 179-185.
Vivienne E. Duggan et al, "Amyloid A in equine colostrum and early milk", Science Direct, Veterinary Immunology and Immunopathology 121, 2008, pp. 150-155.
Written Opinion issued Jun. 8, 2022 in PCT/US2022/015769, 5 pages.
Berg, Lise, C., et al., "Serum amyloid A is expressed in histologically normal tissues from horses and cattle", Veterinary Immunology and Immunopathology, vol. 144, No. 1, Jun. 29, 2011, (Jun. 29, 2011), pp. 155-159, XP028323501.
Ceciliani, F., et al., "Acute phase proteins in ruminants", Journal of Proteomics, vol. 75, No. 14, Apr. 2, 2012, (Apr. 2, 2012), pp. 4207-4231, XP028402451.
Extended European Search Report issued Jan. 24, 2025, in corresponding European Patent Applicaiton No. 22753241.3, 9 pages.

* cited by examiner

*Primary Examiner* — Maureen Wallenhorst
(74) *Attorney, Agent, or Firm* — Element IP, PLC

(57) ABSTRACT

The use of SAA/MAA levels in mammalian fluids to develop management strategies that maximize mammalian health, productivity, and economic return including for example the formulation of cost effective nutritional management strategies, determining whether an individual mammal should be retained in a herd or culled, determining the value of the individual mammal as a contributor of genetic material for herd replacement, determining a course of immediate and/or prophylactic health care intervention, etc.

11 Claims, No Drawings

FLUID MAA/SAA LEVELS AS MAMMAL MANAGEMENT TOOLS

CROSS-REFERENCE TO RELATED APPLICATIONS

This application claims priority to U.S. provisional applications 63/148,789, 63/148,779, 63/148,778, and 63/148,777, all filed Feb. 12, 2021, and to U.S. provisional application 63/290,276, filed Dec. 16, 2021, all of which are fully and completely incorporated herein by reference as if fully written out.

FIELD OF THE INVENTION

As used herein, where the terms “invention,” “the invention,” “the present invention,” and the like appear they refer only to the particular embodiment immediately following. They are not broadly limiting overall, or generally limiting with regard to the several individual advances in the art described herein.

This invention relates in part to mammary associated amyloid A (MAA), to serum associated amyloid A (SAA), to the detection of these substances in mammalian colostrum, mucus, semen, and other fluids as described, to the determination of the amount of these substances in mammalian colostrum, mucus, semen, and other fluids as described, and to the several beneficial ways in which such detection and measurement/quantification can be used to, e.g., develop management strategies that maximize mammalian health, productivity, and economic return including for example the formulation of cost effective nutritional management strategies, determining whether an individual mammal should be retained in a herd or culled, determining the value of the individual mammal as a contributor of genetic material for herd replacement, determining a course of immediate and/or prophylactic health care intervention, etc.

This invention also relates to a method whereby MAA/SAA concentrations are determined in whole colostrum, mucus, semen, and other fluids as described. For example, these colostral concentrations correlate with the concentration of other colostral proteins that are similar in their activities and synthesis pathways. The results indicate the degree of risk of developing enteric disease in the newborn who consumes this colostrum. It allows for a quick intervention in protecting the newborn based upon this risk.

The test for determining the presence and amount of MAA and/or SAA in mammalian fluid used herein preferably allows it to be performed at the point of sample collection or whenever and wherever the use of the test becomes convenient.

This invention also relates to a method that predicts inherent longevity productivity and disease resistance in mammals. The invention accomplishes this through the quantification of the presence of acute phase proteins and other related substances in any bodily fluid such as blood but preferably those fluids produced by the mucosal epithelia of the digestive, respiratory and reproductive tracts. In a preferred embodiment, the 3, 4 and 5 isotypes of the acute phase protein Serum Amyloid A (SAA) are the most sensitive indications of the aforementioned physiologic traits.

This invention also relates to a method whereby Serum Amyloid A (SAA) isotypes 1, 2, 3, 4, and are determined in secretions of mucosal epithelial cells. In the preferred embodiment of this aspect of the invention, semen is the source of those secretions but other sources such as nasal or intestinal secretions are also sources. The isotype concentrations of SAA 1, 2, 3, 4 and 5 correlate with the genetic superiority of the male who was the source of those secretions.

This invention also relates to a method for assessing the innate immunological response in mammals. It involves the quantifying of the acute phase proteins Serum Amyloid A (SAA) and Mammary Associated Amyloid (MAA).

BACKGROUND OF THE INVENTION

While the discussion of the invention will focus on bovine MAA and SAA, all colostrum-producing mammals are included herein, including without limitation alpacas, bison, buffaloes, camels, caribou, cows, domestic cats, deer, domestic dogs, elk (moose), goats, hare, horses, humans, llama, pigs, rabbits, sheep, cattle, etc. Commercial mammalian livestock are particularly preferred. For aspects of the invention related to semen analysis, all mammals are included herein. The values provided herein are generally representative of mammals. Additionally, the techniques described herein regarding testing a population to determine a standard correlation between outcome and MAA/SAA level can be used for any type of mammal to provide a species-specific correlation and an average value or range. Then, values that are above or below the average value by 10, 20, 30, 40, 50, 75, 100, 150, 200, 250, 300, 350, 400, 450, 500, etc. percent can be used as a selection limit determinative of how the tested individual is then utilized.

Serum Amyloid A (SAA) proteins are small (104 amino acids) highly conserved proteins. There are 5 (perhaps 6) isotypes. SAA 1 and 2 are believed to be produced by the liver, while 3, 4 and 5 are believed to be synthesized by mucosal epithelia. All are currently believed to play a critical role in the control and possible propagation of the primordial acute phase response (APR). SAA1 and 2 are present in the blood of healthy individuals (normally found at 20 to 50 Mcg/ml), however these levels can rise as much as 1000-fold within hours after the onset of the APR. Once the APR is resolved, they will rapidly fall to base line levels.

Mammary Associated Amyloid (MAA) was the name given to what was believed to be only the A 3 isotype of SAA by McDonald et.al, see below, who isolated its activity in mammalian colostrum. The N-terminal region of these proteins differ from the hepatically produced serum isotypes 1 and 2. It is also found in milk at levels of less than 10 mgr/ml but will increase with onset of mastitis as part of a localized APR. Just as reported for serum SAA 1 and 2 once the APR is resolved, they rapidly fall to baseline levels.

See, “Serum amyloid A—A Review”, Sack G. H., Molecular Medicine (2018) 24:26 and “Elevated extrahepatic expression and secretion of mammary-associated serum amyloid A 3 (M-SAA3) into colostrum”, T. L. McDonald et al., Vet Immunol Immunopathol, (2001) 83:203-11, both incorporated herein by reference.

Colostrum is a form of breast milk produced by female mammals during the first 24 to 48 hours postpartum. The benefits of colostrums are widely recognized and deemed essential to the neonate for survival. Colstrum provides antibodies which confer passive immunity to neonates, direct bactericidal and bacteriostatic factors which enhance the ability of the neonate to resist pathogenic challenge, and growth factors which help the maturation of the gut, as well as confer higher tissue and repair capabilities. Another important part of the gastrointestinal tract’s defense system is the resident microflora populating the intestinal lumen. Colostrum has prebiotic activity and thus helps balance the intestinal microflora which not only promotes nutrient absorption facilitated by colonic microflora, but lowers the potential for infection, diarrhea and intestinal inflammation.

The quality of colostrum, that is, its effectiveness in protecting the newborn from enteric infection has, until now, been linked solely to its IgG and IgA content. IgG and IgA are antibodies produced by the female and passed to the newborn in colostrum. These antibodies provide protection from infectious disease during the period when the newborn is incapable of producing them for itself. There are two methods commonly used to determine IgG and IgA content and consequently, assumed colostrum quality; directly, using a laboratory-based radio immuno assay and indirectly using either hydrometrics or refraction. There are three problems with these approaches: (1) RIA methodology cannot be done in real time; (2) both the hydrometric and refraction measurements assume specific gravity is positively correlated to colostrum quality as a result of the correlation between specific gravity, protein density and IgG and IgA content and (3) and the most important, is that these methods do not quantify the concentrations of the other key colostral components, proteins which follow a very different synthetic pathway than that for IgA and IgG. Colostrum contains a number of other components that have been shown to be of significant biological value to the newborn. One of these is the protein mammary associated amyloid (MAA).

The MAA A3 as identified and studied by McDonald et al., see above, actually was the 3, 4 and isotypes of SAA. He isolated their activity in mammalian colostrum, and determined them to be acute phase proteins produced by the mammary gland of all mammals whose primary physiologic function is to protect the newborn from enteric infection and catalyze the development and maturation of the neonatal gut. This protein is induced by the hormone prolactin which activates the MAA promoter to actively transcribe the mRNA for translation into the active MAA molecule. MAA is synthesized in the mammary gland of all mammals as a result of mRNA transcription of the MAA promoter by the hormone prolactin. Prolactin is a pituitary hormone that is influential over a large number of physiologic functions, examples of which include playing an essential role in metabolism, stimulating pancreatic development and the innate regulation of the immune system. Perhaps its most widely recognized physiologic function is to stimulate lactogenisis. Prolactin typically increases in the pregnant mammal to high levels (up to 20 times baseline) just prior to parturition.

The gastrointestinal tract is the largest immunological organ in the body of a mammal, working through the coordination of a number of physiologic pathways with one of the most important being the production of site-specific types of mucus. This mucus varies in density and penetrability based upon location. In the small intestine, the primary site of nutrient absorption, mucal penetrability is very high. To compensate, epithelia synthesize a number of proteins that are components of the innate immunological response. Examples include acute phase proteins, various immunoglobulins enzymes and bacteriostatic "defensins." The mode of action will vary with the protein source. For example, defensins employ a feedback mechanism to stimulate the production of a specific type of mucus called mucin 3 which is itself bactericidal. These defensins are also chemo attractants for neutrophiles and macrophages.

Semen, also known as seminal fluid or seminal plasma, is an organic fluid created to contain spermatozoa. It is secreted by the gonads and other sexual organs of male animals and can fertilize the female ovum. In mammals, seminal fluid contains several components besides spermatozoa including proteolytic and other enzymes as well, as fructose, citrate, phosphatase and lipids. Seminal fluid provides a nutritive and protective medium for the spermatozoa during their journey through the female reproductive tract. The normal environment of the vagina is a hostile one for sperm, as it is very acidic, viscous and patrolled by neutrophils and macrophages, key components of the innate immunological response to foreign proteins such as sperm. The components in the seminal fluid attempt to compensate for this hostile environment, by buffering the acidic environment of the vaginal canal. Seminal fluid has also been shown to have viral and bactericidal properties.

Mucus makes up about 1% of the total volume of seminal fluid but is a key component in protecting spermatozoa. It is primarily synthesized in the bulbourethral glands which are themselves lined with mucosal epithelial cells. Mucosal epithelia in the mammary gland of the female will synthesize three unique isotypes of the acute phase protein, serum amyloid A (SAA) 3, 4 and 5, although all isotypes 1 and 2 can be present. This occurs at parturition and again if the mammary gland becomes infected during lactation. All isotypes are biologically of significance, however SAA 3, 4 and 5, are biologically active as chemoattractants for neutrophils and macrophages as well as stimulating mucosal epithelia to produce mucin 3, a mucus that is both bactericidal and bacteriostatic.

Innate immunity is the interplay of signaling molecules with specific cell types the enable a host to recognize and attempt to remove disease causing pathogens that put the host at risk. One example of innate immunity is the systemic reaction of a mammal to an infectious challenge. When challenged with a bacterial infection, leukocytes are released as a primary line of defense. Through the process of phagocytosis, and its related destruction of the cell walls of the engaged infectious bacteria, metabolites that stimulate the release of other proteins that aid in protecting the mammal are also released.

Two of the most important of these are the acute phase proteins, Serum Amyloid A (SAA) produced by the liver and Mammary Associated Amyloid (MAA), produced in the mammary gland of lactating female mammals and concentrated in colostrum, the first milk produced by mammals. Both of these proteins will increase from almost undetectable levels to several thousand fold increase in concentration systemically within a few hours of the initiation of an inflammatory response. Once the insult has been dealt with, their concentrations will return to base line.

BRIEF SUMMARY OF THE INVENTION

The present invention provides, in one embodiment, a solution to the problems encountered with MAA deficiency by providing a method including a rapid, point of care test for MAA in colostrum that determines colostral concentrations of MAA. These MAA levels are also indicative of the concentrations of other essential colostral proteins, thus allowing for an immediate intervention to protect the newborn when this condition is found. This method also indicates the degree of risk of developing enteric disease in the newborn who consumes this colostrum, and allows for a quick intervention in protecting the newborn based upon this risk. Furthermore, this method can also be used for identifying females who need, and are then optionally administered, therapeutic intervention to increase colostrum quality for future pregnancies/births. Additionally, this method identifies females with high quality colostrum, thereby providing information on future genetic selection.

Further, in a study by the inventor in lactating dairy cattle, it was discovered that the concentration of colostral MAA was, surprisingly and unexpectedly, strongly correlated with the subsequent/future lactational performance of the individual lactating cow. This discovery provides the ability to accurately predict the productivity of lactating female mammals at the very initiation of lactation which in turn provides, e.g., highly significant, positive physiologic and economic opportunities in the management of commercial mammalian species. For example, in dairy cattle, projections of lactational output allows for developing management strategies that maximize economic return. Examples include the formulation of cost-effective nutritional management strategies; providing input as to whether an individual should be retained in the herd or culled, and providing input into the assessment of the value of the individual as a contributor of genetic material for future herd replacements. These variables apply to any commercial mammal species but are particularly of value in those species where milk production, whether it is harvested for direct use, or harvested through the marketing of the offspring, is key to commercial success.

Further, in studies conducted by the inventor, it was found that defensins, represented by SAA herein, a key component of innate immunity, are not produced in biologically functional levels in certain animals within species and across species. It was further discovered that there was also a subset population that produced them at 5 to 6 times normal. This subset population was found to be more disease resistant; utilized nutrients more effectively and were able to cope with the challenges presented by their environment more successfully, than the rest of the population. Furthermore, defensin concentration was found to be inherent, maternally linked, and reflective of mitochondrial activity.

Further, it was found by the inventor that SAA 3, 4 and 5 isotypes are found in all mammal mucoid secretions produced by mucosal epithelia. Depending on the secretion, normal concentrations are measured in ng/ml (saliva, and semen) but can reach gr/ml levels in vaginal mucus. These isotypes have been detected at birth (as measured in saliva) and in semen and vaginal mucus, at puberty.

Further, in studies conducted by the inventor, it was found that with dairy cattle some females do not produce SAA including its various isotypes at functional levels, where others were found to produce them at 5 to 6 times normal. This subset population was shown to be more stress resistant as measured by significant increases in milk production, disease resistance, reproductive efficiency and productive longevity as compared to cows that had these proteins expressed at lesser concentrations. It was further discovered that this was not environmentally induced.

Further, in studies conducted by the inventor, it was found that dairy bull semen showed the presence of SAA 3, 4, and 5 with a variance of concentration ranging from low levels (e.g., 135 ng/ml) to levels that were, e.g., 2.25, 3, 4, 5, 6, etc. times greater than a normal/average SAA 3, 4, and 5 level of ca. 225 ng/ml. The bulls that had high isotype levels (e.g., 775 ng/ml SSA 3, 4 and 5) sired daughters who were themselves superior to their herd mates in terms of productivity, fertility, disease resistance and productive longevity as reflected in the records provided by the source of the semen. Thus, SAA semen values of 300, 325, 350, 375, 400, 425, 450, 475, 500, 525, 550, 575, 600, 625, 650, 675, 700, 725, 750, 775, 800, 825, 850, etc. ng/ml are preferred for selecting bulls for reproduction value. Accordingly, once the results of the semen SAA test are known, the value of the individual as a contributor of genetic material for future herd replacements can be assessed and the individual either sold/used for reproduction or put to uses other than reproduction for dairy bulls known in the art.

Further, in studies conducted by the inventor, it was found that the concentration of colostral MAA surprisingly strongly correlates with subsequent rates of clinical mastitis. The inventor has found that both SAA and MAA are predictive of not only the presence of infection, but also the ability to resist infection, as indicated by physiologic performance. Examples include reproductive efficiency (conception rates, successful pregnancies carried to term, neonatal survival postpartum) and lactational performance and measured by milk volume and milk quality.

DETAILED DESCRIPTION OF THE INVENTION

As used herein, with respect to antibodies the term "immunologically specific" refers to antibodies that bind to one or more than one epitope of a protein of interest, but which do not substantially recognize and bind other molecules in a sample containing a mixed population of antigenic biological molecules.

The substances being measured, reported, discussed, and of general interest herein in the colostrum, saliva, semen, mucus, etc., of mammals are primarily Serum Amyloid A (SAA) isotypes 3, 4 and 5 unless otherwise specified. SAA 1 and 2 appear in blood, and do not normally appear in the colostrum, saliva, semen, mucus, etc., of mammals being tested herein in the absence of trauma.

All values, concentrations, amounts, ranges, etc. given and referred to herein, whether identified for MAA or SAA, or for a specific isotype of SAA, represent the sum of all five SAA isotypes (i.e., SAA 1, 2, 3, 4 and 5) present in the fluid being measured/discussed unless otherwise noted. Such values, concentrations, amounts, ranges, etc. are referred to as MAA or SAA values, concentrations, amounts, ranges, etc.

Mammary Associated Amyloid (MAA) is SAA 3 herein, which is a particularly preferred embodiment.

In instances where a specific MAA amount/level/concentration is provided, or a specific SAA amount/level/concentration is provided, or a specific isotype (or group of isotypes) of SAA amount/level/concentration is provided such are preferred embodiments and, as mentioned above, represent the sum of all five of SAA isotypes 1, 2, 3, 4, and 5 present. However, included herein as preferred sub-embodiments are these same amount/level/concentration values for the same indications but applicable to any one and any combination of two, three, or four of SAA isotypes 1, 2, 3, 4, and 5. While these preferred sub-embodiments are not explicitly written out herein, they are included.

As used herein, cattle refer to domesticated mammals of the genus *Bos*. A bull is an in-tact male bovine, a bull calf is a male calf, a calf is a young bovine (this term is used from the time of birth up until about 6 to 10 months of age when the animal is weaned), a cow is a female bovine that has had a calf (this term may also be used for other species), a heifer is a female bovine that has not had a calf, a heifer calf is a female calf, a steer is a castrated male bovine or can be a future ox that is less than 4 years old, an ox is castrated bull that has been trained to work and is at least 4 years of age.

In view of the deficiencies in the art as described above and other related goals well known to the art, one object of the present invention is to provide a test that measures MAA/SAA in whole colostrum, the results of which can be used in several ways as described herein; for example to produce a milking herd by including/not including a given individual, for newborn intervention, for identifying females who need, and are then optionally administered, therapeutic intervention to increase colostrum quality for future pregnancies/births, to predict potential lactational productivity in lactating females, etc.

Another object relates to a method that predicts inherent longevity, productivity, and disease resistance in mammals through the quantification of the presence of acute phase proteins and other related substances in any bodily fluid such as blood but preferably any of those fluids produced by the mucosal epithelia of the digestive, respiratory and reproductive tracts. In a preferred embodiment, all the isotypes of the acute phase protein Serum Amyloid A are the most sensitive indications of the aforementioned physiologic traits.

Another object of the present invention comprises a method for measuring the amount of SAA 3, 4 and 5 in a colostrum sample. Preferably the amount is measured using an immunological assay with antibodies immunologically specific for these isoforms of SAA, optionally including the 1 and 2 forms. Most preferably the test would be a lateral flow point of care test, although any test with similar properties will work.

Another object of the present invention is to provide a test that measures the amount of MAA mRNA in the colostrum sample. Preferably the amount of MAA mRNA is measured using a hybridization assay with nucleic acid molecules, complementary to the MAA mRNA. Amounts given herein for MAA apply to mRNA.

Another object of the present invention is to accurately determine the presence and concentration of all essential colostral components by using MAA as an indicator.

Another object of the present invention is to provide a test that can be quickly and easily performed at the point of sample collection, thus allowing for an immediate response to the risk of enteric disease in the newborn when the colostrum tested is of low quality.

Another object of the present invention is to be able to predict the potential future lactational performance of females using colostral MAA as an indicator.

Another object of the present invention is to provide a method whereby SAA concentrations are correlated with milk production, disease resistance, reproductive efficiency, and productive longevity in females and reproductive performance in males. The test format would preferably allow samples to be tested to be performed at the point of collection, although any method that quantifies SAA concentration is acceptable.

Another object of the present invention is to provide a test that measures SAA in whole blood where in this specific instance the sum of SAA 1, 2, 3, 4, and 5 are measured as SAA 1 and 2 are present in blood, the results of which can be used to characterize and predict the reproductive performance of the individual tested. The test format would allow it to be performed at the point of sample collection, although any method that quantifies SAA concentration in blood is acceptable. The result indicates the ability to conceive and maintain a pregnancy once conception has occurred. Recommended interventions, based on the results, can then be applied, as necessary.

These and other objects may become more apparent to those skilled in the art upon reviewing the subject matter of this invention as detailed herein.

One preferred embodiment herein is a method whereby, given a population of pregnant mammals, the individual's SAA 3, 4 and 5 total concentration is determined in whole colostrum immediately after parturition (e.g., 0-2 days after parturition, preferably from less than 1 hour to not more than 48 hours after parturition). These concentrations are then plotted/compared against measured lactational output at one or several subsequent time periods to provide a correlation (one time period) or several correlations (multiple time periods) specific to that population as well as generally predictive of other populations of the same species. A similar method could be undertaken with a single pregnant mammal, if desired, providing a correlation (one time period) or several correlations (multiple time periods) for that individual, but such a method would provide correlations less predictive of the species as a whole, and less useful overall. The resultant correlation(s) can then be used subsequently to predict the lactational output/estimate the potential productivity of any individual female of the same species based on the amount of SAA 3, 4 and 5 measured in its colostrum. This would also be true for any other quantifiers potentially dependent on milk production measured during correlation formation. Where a population of pregnant mammals is used to form the correlation(s), the greater the number of individuals in the population the better the correlation(s) will be in predicting lactational output, etc. for the species in general. Such correlations are termed "standard correlations." Preferably, the test format would allow SAA to be measured at the point of sample collection, although any method that quantifies SAA concentration in colostrum is acceptable.

Once a standard correlation is available, for example a standard lactational output correlation for dairy cows (see, e.g., Table 1 infra), it can be used to characterize a given individual based on the amount of SAA in its colostrum, for example used to predict its overall lactational output. Moreover, once an individual dairy cow has its colostral SAA measured and is characterized by comparison to a standard lactational output correlation, it can be managed in several ways. For example, individuals with low predicted overall lactational output based on their colostral SAA level could be culled from a given milking population, individuals with high predicted overall lactational output could be allowed to remain, be added to, or used to form a "super" milking population, etc.

The implications of this predictive ability of colostral SAA level on the management of commercial mammalian species is enormous. For example, in dairy cattle, projections of lactational output allows for developing management strategies that maximize economic return. Examples include the formulation of cost-effective nutritional management strategies; providing input as to whether an individual should be retained in the herd or culled, and providing input into the assessment of the value of the individual for sale and/or as a contributor of genetic material for future herd replacements. In all such instances decisions as to how to use, or not use, the tested individual are based, at least in part, on the level of SAA in the individual's colostrum.

Referring now to an exemplary embodiment of the invention, colostrum is analyzed for the presence and the amount of SAA as a diagnostic test for, e.g., quality of the colostrum, future productivity, etc. The assays of the invention comprise providing a test sample of colostrum and measuring for the presence and concentration of SAA. This would then be compared against a standard SAA concentration already known to be adequate, determined for example from a standard correlation.

Any assay that detects and quantifies SAA in a sample is contemplated for use in the present invention. Two categories of assays are preferred. One is an immunological assay for SAA protein and the other is a hybridization assay for mRNA encoding SAA protein, although in the preferred embodiment of the invention, this assay would use an immunologically specific antibody for SAA in a lateral flow format that would be performed at the point of sample collection.

The results of the assay, i.e., colostrum SAA concentration, may be used to predict colostrum quality, subsequent lactational productivity of the tested female, etc. Currently, colostrum quality is determined by one of three methods; radial immunodiffusion, which measures only the presence of Immunoglobulin G, an antibody present in colostrums, hydrometrically, which measures the concentration of proteins as a whole by specific gravity, and refractometry, which measures total solids in solution. The problem with all these methods is that they are either indirect or laboratory based or assay for only one protein, IgG. IgG and IgA are not correlated in any way with any of the other essential colostral proteins, all of which are prolactin induced and produced in the mammary gland. Thus, conventional colostrum testing leads to inaccurate and even dangerous assessment of colostrum quality.

Moreover, none of these methods is predictive of potential milk synthesis, a key function of the hormone prolactin. Only through the quantitative measurement of the prolactin induced proteins found in milk and of even greater significance, their presence in colostrum, is it possible to predict the outcome of prolactin activity.

Any assay that detects and quantifies SAA in a sample is contemplated for use in the present invention. Two categories of assays are preferred. One is an immunological assay for SAA protein and the other is a hybridization assay for mRNA encoding SAA protein, although in the preferred embodiment of the invention, this assay would use an immunologically specific antibody for SAA in a lateral flow format that would be performed at the point of sample collection.

The results of the assay, i.e., colostrum SAA/MAA concentration, may be used to predict colostrum quality, subsequent lactational productivity of the tested female, etc. Currently, colostrum quality is determined by one of three methods; radial immunodiffusion, which measures only the presence of Immunoglobulin G, an antibody present in colostrums, hydrometrically, which measures the concentration of proteins as a whole by specific gravity, and refractometry, which measures total solids in solution. The problem with all these methods is that they are either indirect or laboratory based or assay for only one protein, IgG. IgG and IgA are not correlated in any way with any of the other essential colostral proteins, all of which are prolactin induced and produced in the mammary gland. Thus, conventional colostrum testing leads to inaccurate and even dangerous assessment of colostrum quality.

In a preferred embodiment of the invention, for colostrum concentrations of SAA of less than 150 mcg/ml in dairy cows, animals should be culled. Calves from these cows should be provided supplementation, both nutritional and prophylactically to address issues with conditions that could lead to an APR event. If retained in the herd, these cows to be profitable require a different management strategy then currently recognized by experts in the field as accepted practice for animals less than 180 days in production. For other species showing concentrations of SAA 3, 4 and 5 of less than 150 mcg/ml: in species kept to produce dairy products (e.g., goats, buffalo) these should be culled. Again, neonates will require nutritional supplementation etc., as above.

In a preferred embodiment of the invention, for colostrum at SAA concentrations greater than 300 mcg/ml in all species, this level is associated with significant increases in productivity, fertility and stress resistance when compared to other individuals.

This invention also relates to a method that predicts inherent longevity, productivity, and disease resistance in mammals. The invention accomplishes this through the quantification of the presence of acute phase proteins and other related substances in any bodily fluid such as blood but preferably those fluids produced by the mucosal epithelia of the digestive, respiratory and reproductive tracts. In a preferred embodiment, all the isotypes of the acute phase protein Serum Amyloid A are the most sensitive indications of the aforementioned physiologic traits.

Thus, in another exemplary embodiment of the invention, any bodily mammalian bodily fluid such as blood but preferably any one or more of those fluids produced by the mucosal epithelia of the digestive, respiratory and reproductive tracts is analyzed for the presence and the amount of Serum Amyloid A (SAA) as a diagnostic test for, e.g., inherent longevity, productivity, and disease resistance, etc. The assays of the invention comprise providing a test sample and measuring for the presence and concentration of SAA. This would then be compared against a standard SAA concentration or known SAA average for the species. Values that are 2.5, 3, 4, 5, or 6 times or more greater than the average SAA concentration for the given specie indicate a superior individual, and such characterization can be used to make decisions regarding future genetic use/selection. Any assay that detects and quantifies SAA in a sample is contemplated for use in the present invention.

In another exemplary embodiment of the invention, seminal plasma is analyzed for the presence and the amount of any one or more than one isotype of Serum Amyloid A (SAA), particularly one or more of SAA 3, 4, and 5, as a diagnostic test for, e.g., being a superior sire. The assays of the invention comprise providing a test sample and measuring for the presence and concentration of SAA. This would then be compared against a standard SAA concentration or known SAA average for the species. Values that are 2.5, 3, 4, 5, or 6 times or more greater than the average SAA concentration for SAA 3, 4, and 5 for the given specie indicate a superior individual, and such characterization can be used to make decisions regarding future genetic use/selection, such as breeding. Any assay that detects and quantifies SAA in a sample is contemplated for use in the present invention.

In another exemplary embodiment of the invention, elevated levels of SAA 1 and 2 (i.e., SAA present in blood) have been shown by the inventor to be correlated negatively with reproductive efficiency as measured by conception rates, and services per conception in a mammalian species. Specific examples include bovine, equine, porcine and canine females, but similar results would be provided for any female mammal. Elevated levels have also been shown to be associated negatively with the maintenance of a pregnancy to term as well as the post-partum viability of the neonates themselves. The inventor has successfully quantified and differentiated SAA levels that are indicative of reproductive failure, however measured, so that they become accurately diagnostic and can be easily distinguished from other events that can also illicit an SAA systemic response. SAA values (serum titers) greater than 30, preferably greater than 45, 50, 60, 70, 80, 90, 100, 150, and 200 ug/ml, and especially SAA values greater than 250 ug/ml, predict poorer reproductive efficiency. SAA values (serum titers) less than 45, less than 30, less than 25, less than 20 ug/ml, etc. predict good reproductive efficiency.

In dairy cows, calf saliva SAA concentrations less than 200 ng/ml reflects/predicts a future poor performer—i.e., a cow with colostrum scores of less than 150 mcg/ml. Such calves can, e.g., be excluded form a milking herd, given nutritional interventions, etc. SAA calf saliva at concentrations of greater than 400 ng/ml reflects a future 300 mcg/ml+in colostrum performance. Such calves can be included in a milking herd, et.

EXAMPLES

The testing in the following examples was done using the ELISA test described in "Elevated extrahepatic expression and secretion of mammary-associated serum amyloid A 3 (M-SAA3) into colostrum", T. L. McDonald et al., Vet Immunol Immunopathol, (2001) 83:203-11, incorporated herein by reference.

In one study, colostrum was collected at the first milking from dairy cows of the Brown Swiss and Jersey breeds. The cows were independently housed and managed as separate herds. Colostrum samples were collected at the first milking from all four quarters of the mammary glands of each individual and composited for that individual. Samples were then frozen and later analyzed for SAA. Three distinct populations based upon SAA concentration where found to exist: cows that synthesized low levels of SAA (<150 ugr/ml); cows that produced moderate levels of SAA (150 to 300 ugr/ml); and cows that produced elevated levels of SAA (>300 ugr/ml). The milk production of all cows was then monitored throughout the subsequent lactation.

Surprisingly, productivity was reflected in colostral SAA concentration at first milking: cows within the low (<150 ug/ml) group were the least productive with an average production of 25,762 lbs The cows who synthesized SAA in the moderate range of 150 to 300 ugr/ml, produced an average of 26,220 lbs or 458 lbs more milk, while the elevated group produced an average of 28,600 lbs, or 2380 lbs more than the moderate group and 2838 lbs more than the lowest group. These data are summarized in Table 1. Samples were taken within 12 hours postpartum, stored and frozen, and assayed for SAA by quantitative ELISA.

TABLE 1

SAA Concentration in Colostrum and Subsequent Lactational Performance in Dairy Cows

| | SAA levels (ugr/ml) | | |
|---|---|---|---|
| Number of females | (<150) | (150-300) | (>300) |
| 34 | 25,762lbs | | |
| 57 | | 26,220lbs | |
| 25 | | | 28,600lbs |

These results show that, for dairy cows, colostral SAA concentrations of at least 150 micrograms per milliliter (ugr/ml) provide desirable milk production, while those having colostral SAA concentrations of less than 150 ugr/ml are far less desirable. Dairy cows can thus be characterized as efficient milk producers, and considered to produce high quality colostrum, if they have colostral SAA concentrations of at least 150 ugr/ml, preferably greater than 200 ugr/ml, including without limitation 175, 200, 225, 250, 300, 325, 350, 375, 400, 425, 450, 475, 500, etc. micrograms per milliliter. Decisions regarding nutritional management strategies for both the individual and the offspring, determining whether an individual should be retained in the milking herd or culled, and determining the value of the individual for sale and/or as a contributor of genetic material for future herd replacements can reliably be made based on these SAA concentrations. SAA concentrations of 200 ugr/ml are preferred for dairy cows to remain in a milking herd, reproduce, etc.

The incidence of clinical mastitis as indicated by treatment was also monitored throughout lactation. In cows within the lowest concentrations of SAA (<150 ug/ml), 50% had to be treated sometime during the lactation with 30% of that population having more than one treatable bout. The cows who synthesized SAA in the moderate range of 150 to 300 ugr/ml only had a clinical, treatable incidence of 16% of which 40% had repeat infections. In the elevated group, mastitis affected 70% of the population, although surprisingly, these cows were also the highest producers. Also only 16% of the infected animals had a recurrence of the infection after initial treatment.

In another similar study 375 cows involving three breeds of primiparous and multiparous cows were used. The study group consisted of Holstein, Jersey, and Brown Swiss breeds that were managed independently at three different locations. Colostrum samples were harvested within 12 hours postpartum from each previously stripped quarter, pooled and then analyzed. Concentrations of SAA fell into three distinct ranges: less than 150 ug/ml; 150 to 300 ug/ml and greater than 300 ug/ml. Three parameters were used in assessing animal performance in this study: 1) lactation performance reported as fat corrected milk (FCM), 2) documented cases of clinical mastitis and 3) the success or failure of treatment of the clinical cases. The following was determined:

TABLE 2

| Application | SAA | | |
|---|---|---|---|
| Colostrum Concentration of Individual Pooled Samples at 12 hrs Postpartum | <150 ug/ml<br>93/375 | 150-300 ug/ml<br>227/375 | >300 ug/ml<br>63/375 |
| Colostrum Quality | Poor | Adequate | Adequate |
| Risk of Neonatal Clinical Disease | High Risk | Normal Risk | Normal Risk |

TABLE 2-continued

| Application | SAA | | |
|---|---|---|---|
| Mastitis Incidence in the Subsequent Lactation | 45%[a] 42/94 | 8%[b] 19/241 | 68%[c] 27/40 |
| Percentage of Cows with Multiple Clinical Bouts of Mastitis | 30%[a] | 30%[a] | <10%[b] |
| Milk Yield, 1b FCM** | 24,128[a] | 27,781[b] | 29,434[c] |
| Example Management Decisions that Could be Based on Colostral SAA Concentrations | Cull | Monitor Strategic Therapeutic Approach to Mastitis Control | Selection/Breeding Strategic Therapeutic Approach to Mastitis Control |

*375 cow study involving three breeds of primiparous and multiparous cows.
**Means with different superscripts are different at the P < 0.01.

The animals that had the lowest (<150 ug/ml) SAA titers averaged 10,967 kg of FCM. This group also had a 45% incidence of clinical mastitis (42/94) of which 30% of the effected animals (13 cows) required repeated treatment or were culled from the herd as a result of that infection. The 150-300 ug/ml population averaged 12,627 kg of FCM with a clinical mastitis reported in 8% (19/227) of the animals and with a repeated treatment rate of 30% (6 cows). The third population with SAA concentrations greater than 300 ug/ml in their colostrum, averaged 13,379 kg of FCM, 749 kg more milk than the 150-300 ug/ml group and 2,412 kg more milk than the group of animals below 150 ug/ml. This high SAA group also experienced the highest incidence of clinical mastitis, 66% (42/63), however only 4 cows (<10%) needed repeat treatment compared to 30% in the other two groups. When the data from the 126 primiparous cows were compared as a subset group to the entire study group of animals, they had similar responses in milk yield and mastitis incidence and response to treatment that was found reported for the study population as a whole. This indicated that cows with signal or multiple pregnancies was not a factor in regulating SAA production. Breed differences were not a contributing factor that may have influenced the three different colostrum SAA concentration groups, although this observation does not preclude a genetic component being a factor in determining an animal's ability to synthesize SAA.

In another study, the blood of 75 Irish dairy cattle was tested for SAA (SAA 1 and 2) and reproductive efficiency was studied.

TABLE 3

| Application | SAA | | |
|---|---|---|---|
| Serum Amyloid A Titer at the time of first insemination** | <45 ug/ml 18/75 | 45 to 250 ug/ml 38/75 | >250 ug/ml 19/75 |
| Average Rectal Palpation Score 1 to 5 | 3 | 3 | 4 |
| Days to First Service*** | 65[a] | 81[b] | 92[c] |
| Conception Rate at First Service*** | 60%[a] 10/18 | 38%[b] 14/38 | 15%[c] 3/19 |

*75 multiparous cows of mixed breeding
**Average SAA level for this herd is 131 ug/ml
***Means with different superscripts are different at the P < 0.01.

In a preferred embodiment, SAA concentrations above 200 ugr/ml form a preferred subset of SAA values, indicating good colostral quality, adequate SAA activity, and milk production.

In a preferred embodiment, it has been found that three distinct populations based upon SAA concentration (low levels of SAA (<150 ugr/ml); moderate levels of SAA (150 to 300 ugr/ml); and elevated levels of SAA (>300 ugr/ml)) are predictive of several outcomes including colostrum quality, risk of neonatal clinical disease, mastitis incidence in subsequent lactation, and milk yield. Overall, for the low level producing individual, culling is the preferred management action. For the moderate level producer, targeted monitoring for signs of mastitis is advised as well as a strategic therapeutic approach to mastitis control, and for the elevated producers selection and breeding are recommended as well as targeted monitoring for signs of mastitis and a strategic therapeutic approach to mastitis control.

In another study, semen from 50 dairy bulls was collected and analyzed for SAA content. Surprisingly, no detectable SAA 1 and 2 was found. However, SAA 3, 4, and 5 were present, with a variance of concentration ranging from low levels to levels that were 5 to 6 times greater than normal/average. The bulls that had high isotype levels (i.e., 2.5, 3, or 4, or 5, or 6 times or more greater than the average SAA concentration) sired daughters who were themselves superior to their herd mates in terms of productivity, fertility, disease resistance and productive longevity as reflected in the records provided by the source of the semen.

In another study, confirmed conception rates were determined in 90 Holstein cows and plotted against blood levels of SAA1 and 2 at 120 days post partum. Twelve cows had elevated levels of SAA1 and 2 (>80 ug/ml) which indicates APR. None of these cows had conceived. Fifty eight cows had blood levels of SAA1 and 2 were between 30 and 80 ug/ml, which suggests low grade inflammation. In this group, only 10 (17%) were confirmed pregnant. The remaining twenty cows had blood levels <30 ug/ml, indicative of a none inflammatory state. Fourteen or 56% were confirmed pregnant. Poor reproducers can be utilized in art-recognize ways other than breeding, for example.

The several tests described herein can be performed in the particularly preferred fluids described above as well as in any or all of semen, mucus, saliva, and colostrum and, if SAA 1 and 2 are of interest, blood.

The several invention measurements described herein provide, in general, ways in which to select an individual for the particular indication discussed (e.g., milk production, reproduction, etc.) Those individuals not showing good results generally are not selected for the given indication or are treated prior to and/or during inclusion. Examples of what can be done with non-elected individuals have been provided, and further examples follow.

While the results of the invention test/measurement in semen, mucus and saliva are independent of age, the management strategies adopted as a result of outcome vary with age. In neonates (these would be saliva tested) low scoring animals either bulls or heifers could be culled at any time for veal production, or at the appropriate age (e.g., 6 months to a year) they would be sent to feedlots to be fed out and processed for beef. In dairy cows (saliva, mucus and colostrum) they could be culled and processed for beef or enter into the milking herd but nutritionally managed by feeding diets formulated to meet the nutrient requirements for their projected low production. In today's economy diets fed to early lactation cows cost about $12.00 per head per day. Maintenance diets, which is all that would be required for low scorers (low future producers) however cost about $6.00 per head per day. In dairy bulls (saliva, mucus or semen), they could culled and processed for beef. In beef cows (saliva, mucus or colostrum) they could be culled and fed out for beef. In beef bulls (saliva, mucus or semen) they could be culled and fed out for beef. Animals who have elevated levels of SAA in the blood are being challenged by some inflammatory insult and are manifesting APR. They require medical intervention.

Examples of preferred embodiments described and enabled herein are as follows:

1. A method of producing a mammal milking herd, comprising:
   obtaining or having obtained a sample of colostrum from an individual female;
   performing or having performed a measurement of the amount of SAA in the sample; and
   including the individual female in the milking herd if the concentration of SAA in the sample is at least 150 ugr/ml, or
   excluding the individual female from the milking herd if the concentration of SAA the sample is less than 150 ugr/ml.
2. The method of Embodiment 1, wherein the individual female is excluded from the milking herd and subsequently processed for beef.
3. The method of Embodiment 1, where the female is a dairy cow.
4. A method of mammal breeding, comprising:
   obtaining or having obtained a sample of semen from an individual intact male;
   performing or having performed a measurement of the amount of SAA in the sample; and inseminating a female with the semen of the individual intact male if the concentration of SAA in the sample is at least 300 ng/ml, or
   not inseminating a female with the semen of individual intact male if the concentration of SAA in the sample is not at least 300 ng/ml.
5. The method of Embodiment 4, wherein the intact male is a bull and the female is a cow or heifer.
6. A method of producing a mammal milking herd, comprising:
   including an individual female in the milking herd if the concentration of SAA in the individual female's colostrum is at least 150 ugr/ml, and/or
   excluding the individual female from the milking herd if the concentration of SAA the individual female's colostrum is less than 150 ugr/ml.
7. A method of mammal breeding, comprising:
   inseminating a female with the semen of an individual intact male if the concentration of SAA in the semen of the intact male is at least 300 ng/ml, and/or
   not inseminating a female with the semen of individual bull if the concentration of SAA in the semen of the intact male is not at least 300 ng/ml.
8. A method of evaluating a mammal for breeding, comprising:
   reviewing the SAA level of an intact male's semen and if it is at least 300 ng/ml designating it for breeding and/or breed it and/or sell it optionally for an increasing price with increasing semen SAA level.
9. A method of evaluating a mammal for milking, comprising:
   reviewing the SAA level of a female's colostrum and if it is at least 150 ugr/ml designate it for milking and/or breed it and/or sell it optionally for an increasing price with increasing colostral SAA level.
10. A method of evaluating the value and future performance (for example for milk production, for conception/reproduction, as a contributor of genetic material for future herd replacements, etc.) of a mammal newborn (e.g., 0-21 days), comprising:
    reviewing the SAA level of one or more of the newborn's SAA—containing fluids other than blood (e.g., saliva, mucus) and if it is less than 200 ngr/ml (e.g., less than 175, 150, 125, 100, 80, 60, 40, ngr/ml etc.) designate it for culling.
11. A method of evaluating the value and future performance (for example for milk production, for conception/reproduction, as a contributor of genetic material for future herd replacements, etc.) of a mammal of any age, comprising:
    reviewing the SAA level of the mammal's saliva, and if it is less than 200 ngr/ml (e.g., less than 175, 150, 125, 100, 80, 60, 40, ngr/ml etc.) designate it for culling.
12. A method of evaluating the value and future performance (for example for milk production, for conception/reproduction, as a contributor of genetic material for future herd replacements, etc.) of a mammal of any age, comprising:
    reviewing the SAA level of the mammal's saliva or semen, and if it is less than 200 ngr/ml (e.g., less than 175, 150, 125, 100, 80, 60, 40, ngr/ml etc.) designate it for culling.
13. A method of evaluating the value and future performance of a mammal of any age, comprising:
    reviewing the SAA level of the mammal's saliva or semen, and if it is less than 200 ngr/ml, designate it for culling.
14. The method according to Embodiment 13, wherein the mammal is a calf, the SAA level of the calf's saliva is tested, and wherein if the SAA level of the saliva is greater than 200 ngr/ml the calf is used for at least one of milk production, for conception/reproduction, and as a contributor of genetic material for future herd replacements.
15. The method according to Embodiment 13, wherein the mammal has reached puberty, and wherein if the SAA level of the saliva or semen is greater than 200 ngr/ml the mammal is used for at least one of milk production, for conception/reproduction, and as a contributor of genetic material for future herd replacements.

When an amount, concentration, or other value or parameter is given as a range, or a list of values, herein this is to be understood as specifically disclosing all ranges formed from any pair of any upper and lower values, and all integers and fractions within the range, regardless of whether ranges, all integers, and fractions are separately disclosed. Where a range of numerical values is recited herein, unless otherwise stated, the range is intended to include the endpoints thereof, and all integers and fractions within the range. It is not intended that the scope of the present invention be limited to the specific values recited when defining a range.

The above written description of the invention provides a manner and process of making and using it such that any person of ordinary skill in the relevant art is enabled to make and use the same, this enablement being provided in particular for the subject matter of the appended claims, which make up a part of the original description. This description is provided in the context of a particular application and its requirements. Various modifications to the embodiments will be readily apparent to those of ordinary skill in the relevant art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method of cattle breeding, comprising:

obtaining or having obtained a sample of semen from an individual intact male;

performing or having performed a measurement of the concentration of serum associated amyloid A (SAA) in the sample; and either:

inseminating a female with the semen of the individual intact male if the concentration of SAA in the sample is at least 300 ng/ml, or not inseminating a female with the semen of individual intact male if the concentration of SAA in the sample is not at least 300 ng/ml and optionally processing the intact male for beef, wherein the intact male is a bull and the female is a cow or heifer.

2. The method of claim 1, wherein the concentration of SAA in the sample is 300-850 ng/ml and the female is inseminated with the semen of the individual intact male.

3. The method of claim 1, wherein the concentration of SAA in the sample is 350-850 ng/ml and the female is inseminated with the semen of the individual intact male.

4. The method of claim 1, wherein the concentration of SAA in the sample is 400-850 ng/ml and the female is inseminated with the semen of the individual intact male.

5. The method of claim 1, wherein the concentration of SAA in the sample is at least 400 ng/ml and the female is inseminated with the semen of the individual intact male.

6. The method of claim 1, wherein the concentration of SAA in the sample is at least 500 ng/ml and the female is inseminated with the semen of the individual intact male.

7. The method of claim 1, wherein the concentration of SAA in the sample is at least 600 ng/ml and the female is inseminated with the semen of the individual intact male.

8. The method of claim 1, wherein the concentration of SAA in the sample is not at least 300 ng/ml and the female is not inseminated with the semen of the individual intact male.

9. The method of claim 8, wherein the female is not inseminated with the semen of the individual intact male and is processed for beef.

10. The method of claim 1, wherein the female is a cow.

11. The method of claim 1, wherein the female is a heifer.

* * * * *